United States Patent
Carencotte et al.

(10) Patent No.: US 6,743,946 B1
(45) Date of Patent: Jun. 1, 2004

(54) METHOD FOR SEPARATING HYDROXYMETHYLTHIOBUTYRIC ACID

(75) Inventors: Frédéric Carencotte, Meyzieu (FR); Michel Garrait, Millery (FR); Georges Gros, Antony (FR)

(73) Assignee: Adisseo Ireland Limited, Dublin (IE)

( * ) Notice: Subject to any disclaimer, the term of this patent is extended or adjusted under 35 U.S.C. 154(b) by 0 days.

(21) Appl. No.: 09/743,288

(22) PCT Filed: Jul. 7, 1999

(86) PCT No.: PCT/FR99/01636
§ 371 (c)(1),
(2), (4) Date: Mar. 12, 2001

(87) PCT Pub. No.: WO00/02853
PCT Pub. Date: Jan. 20, 2000

(30) Foreign Application Priority Data

Jul. 10, 1998 (FR) .............................................. 98 08874

(51) Int. Cl.[7] ....................... C07C 381/00; C07C 53/00; C07C 51/16
(52) U.S. Cl. ........................ 562/581; 562/512; 562/526
(58) Field of Search ................................. 562/512, 581, 562/526

(56) References Cited

U.S. PATENT DOCUMENTS

| | | | | | |
|---|---|---|---|---|---|
| 2,745,745 | A | * | 5/1956 | Blake et al. | 514/557 |
| 4,310,690 | A | * | 1/1982 | Cummins | 562/581 |
| 4,353,924 | A | * | 10/1982 | Baker et al. | 424/317 |
| 4,524,077 | A | * | 6/1985 | Ruest et al. | 514/557 |
| 4,579,962 | A | * | 4/1986 | Takano | 556/131 |
| 5,386,056 | A | * | 1/1995 | Matsuoka | 562/526 |
| 5,498,790 | A | * | 3/1996 | Grendel et al. | 562/581 |
| 5,763,652 | A | * | 6/1998 | Kawabe et al. | 562/512 |

* cited by examiner

Primary Examiner—D. Margaret Seaman
Assistant Examiner—Taylor V Oh
(74) Attorney, Agent, or Firm—Connolly Bove Lodge & Hutz LLP

(57) ABSTRACT

The invention concerns an improved method for separating hydroxymethylthiobutyric acid by neutralising hydroxymethylthiobutyronitrile sulphuric hydrolysate, decanting and treating each phase with an organic solvent.

23 Claims, 1 Drawing Sheet

METHOD FOR SEPARATING HYDROXYMETHYLTHIOBUTYRIC ACID

Figure 1:
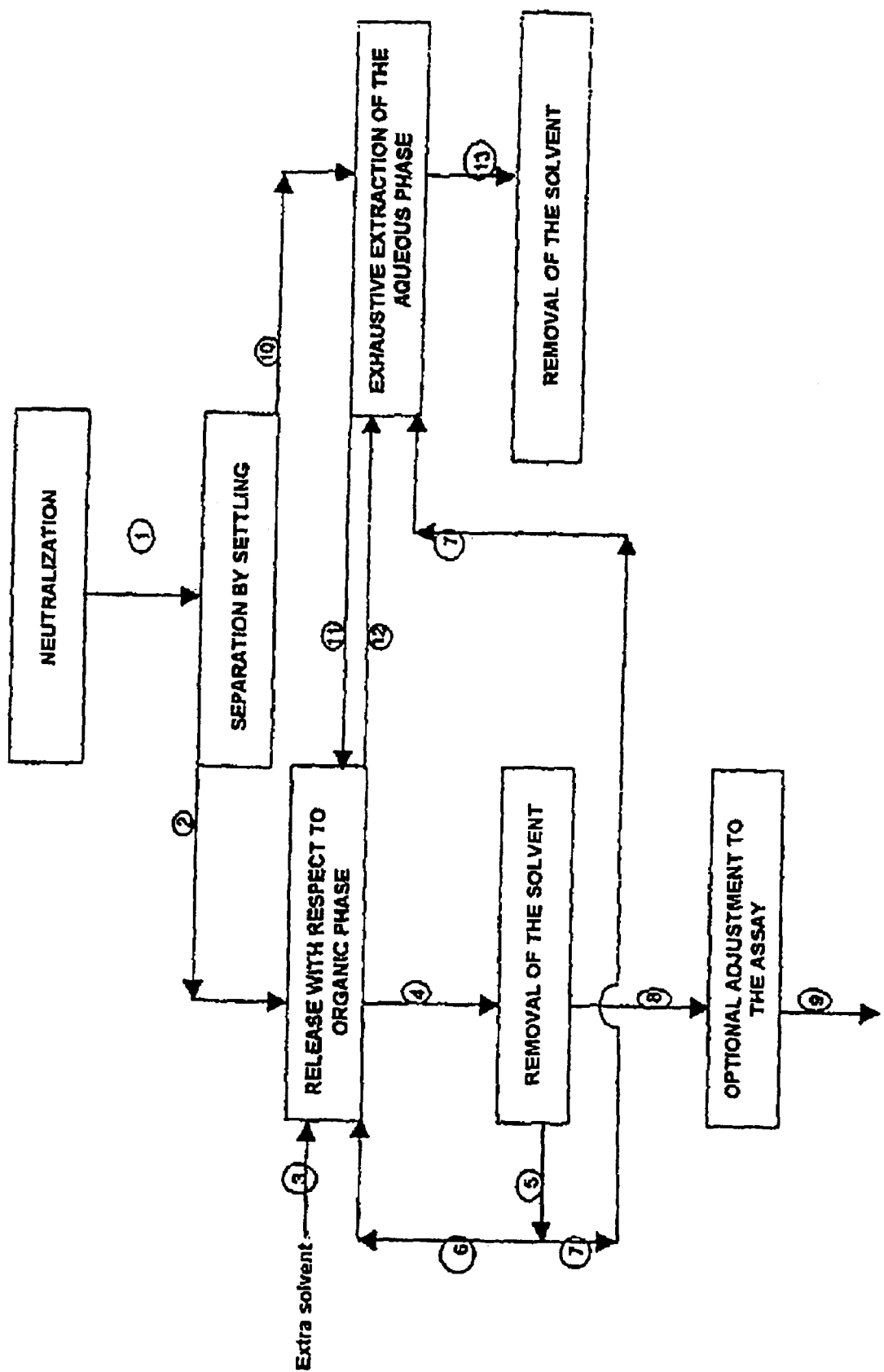

The present invention relates to an improved process for the preparation of 2-hydroxy-4-methylthio-butyric acid (HMTBA) in the form of an aqueous solution and more especially to a process for improved separation from a 2-hydroxy-4-methylthiobutyronitrile (HMTBN) acid hydrolysate mixture. 2-Hydroxy-4-methylthiobutyric acid, an analog of 1-methionine, is used in animal nutrition.

Cummins discloses, in U.S. Pat. No. 3,773,927, a process in which HMTBA is produced by hydrolysis of HMTBN with hydrochloric acid under conditions such that the suspension produced comprises solid ammonium chloride, which is removed by centrifuging. The filtrate is subsequently vacuum distilled to remove the water. This U.S. Pat. No. 3,773,927 discloses a process for the preparation of an aqueous liquid product with a high concentration of HMTBA acid (85 to 90% by mass). This type of product, obtained by such a process, has a strong smell and a dark color and comprises ester oligomers. These characteristics are probably due to the high temperature conditions applied to a product with a low water content during the final dehydration stage. The other disadvantages of this process are a high energy consumption during the same stage and difficulties and losses in yields during the centrifuging or the filtration.

U.S. Pat. No. 2,745,745 discloses the separation of HMTBA by extraction with a water-immiscible organic phase, such as diethyl ether. British Patent No. 915 193 discloses a process for the preparation of calcium salts of HMTBA where the latter is extracted with an ether, such as isopropyl ether or butyl ether, having a boiling point greater than that of ethyl ether. Water is added to form an emulsion, to which calcium carbonate or calcium hydroxide is added to precipitate the calcium salt of HMTBA. This patent does not relate to the preparation of liquid products comprising essentially HMTBA.

Gielkens mentions, in U.S. Pat. No. 3,175,000, that the direct extraction of HMTBA from the hydrolysate gives poor yields. In this patent, the extraction is only used as a secondary recovery means.

U.S. Pat. No. 4,524,077 discloses the liquid-liquid extraction of HMTBA by a water-immiscible organic solvent, preferably methyl isobutyl ketone, and then the recovery of the HMTBA from the extract obtained comprising a minimum of 5% by weight of water on the basis of the mass of HMTBA recovered. The product thus prepared has a lighter color, less of a smell, a lower viscosity and a better thermal stability than the products prepared by the conventional processes described above.

Patent EP 0 330 527 discloses a process for the separation of HMTBA which consists in forming two phases by addition of aqueous ammonia to the hydrolysis solution, each of the phases, the first organic phase comprising the HMTBA and the second aqueous phase comprising the ammonium salt, are subsequently subjected to an evaporation operation, so as to remove the water. The concentrated filtered organic phase is subsequently diluted, so as to adjust its concentration to that of the commercial solution. The ammonium sulfate obtained from the aqueous phase is contaminated by sulfur residues, it often exhibits an unpleasant smell which makes it difficult to sell or which requires additional treatments in order to remove the smell therefrom. The present process requires a large amount of energy during the evaporation of the water from each of the phases obtained after neutralization and an additional treatment stage for the ammonium sulfate, which is also expensive. The present invention has made it possible to solve the abovementioned problems.

DESCRIPTION OF THE INVENTION

The present invention relates to a novel process for the preparation of 2-hydroxy-4-methylthiobutyric acid (HMTBA) and more specifically to a novel process for the separation of HMTBA. This process consists, in a first stage, in adding a neutralizing agent, composed of ammonium hydroxide, to the solution from the hydrolysis with sulfuric acid of 2-hydroxy-4-methylthiobutyronitrile, which results in the separation of the medium into two phases. These two phases are composed of an organic phase, which is subjected to a stage of release of the salts by addition of an organic solvent, and of an aqueous phase, from which residual 2-hydroxy-4-methylthio-butyric acid is exhaustively extracted by addition of an organic solvent.

The system for release of the salts from the organic phase is composed of the addition of a solvent which is not very miscible with water. Mention may be made, among these solvents, of any solvent, chemically compatible with the medium and exhibiting little affinity for water, which makes it possible to dissolve the HMTBA. They can be chosen from ketones, aldehydes, ethers, esters, carbonates or alcohols. They are preferably ketones of low molecular weight, such as methyl ethyl ketone or methyl isobutyl ketone (MIBK), or ethers, such as methyl tert-butyl ether or diisopropyl ether, or carbonates, such as diethyl carbonate. They are more preferably methyl ethyl ketone, methyl isobutyl ketone and ethyl carbonate.

The system for exhaustively extracting the HMTBA from the aqueous phase is composed of the addition of a solvent which is not very miscible with water. Mention may be made, among these solvents, of any solvent, chemically compatible with the medium and exhibiting little affinity for water, which makes it possible to dissolve the HMTBA. They can be chosen from ketones, aldehydes, ethers, esters, carbonates or alcohols. They are preferably ketones of low molecular weight, such as methyl ethyl ketone or methyl isobutyl ketone (MIBK), or ethers, such as methyl tert-butyl ether or diisopropyl ether, or carbonates, such as diethyl carbonate. They are more preferably methyl ethyl ketone, methyl isobutyl ketone and ethyl carbonate.

Each of the stages, release of the salts from the organic phase and exhaustive extraction of the aqueous phase, can be carried out independently of one another or can be carried out jointly during the implementation of the process for the isolation of the HMTBA. It is preferable to carry out these two stages jointly and in a continuous process.

In the case where it is desired to release the salts from the organic solution of HMTBA, the amount of organic solvent which is added to the organic medium composed of HMTBA is according to a solvent/organic solution of HMTBA ratio by weight preferably of greater than 0.3 and more preferably still of between 0.3 and 1. It is obvious that a person skilled in the art will adjust the amount of solvent to be used to the structure of the process. The temperature at which the release is carried out is compatible with the nature of the solvent used and in particular lies below its boiling point.

In the case where it is desired to exhaustively extract the HMTBA from the aqueous solution, it is preferable, according to a better way of implementing the invention, to use an amount of organic solvent with respect to the aqueous solution comprising the inorganic salts, in particular ammonium sulfate, drawn up according to an amount by weight of greater than 0.05 and preferably of between 0.1 and 0.5. The temperature at which the exhaustive extraction is carried out is compatible with the nature of the solvent used and in particular lies below its boiling point.

The following stage consists in evaporating the organic solvent(s) used, which can be alike in the two stages or different. This operation requires less energy than the operation for the removal of water carried out in the prior art.

After evaporation of the solvent or solvents, which are optionally recycled for a fresh operation, an organic phase is obtained which comprises little water and which comprises a greatly reduced amount of salts, which eliminates the filtration phase carried out previously. The phase is subsequently adjusted to the commercial assay of 88% by weight by addition of the water needed.

After two-phase separation between the organic solvent for exhaustive extraction and the aqueous phase comprising the salts, a solution of salts and predominantly of ammonium sulfate is obtained, which solution is crystallized and comprises virtually no more organic contaminants. The crystals are of better quality and exhibit virtually more smells. According to a first means of giving added value to these salts, these crystals are used in particular as fertilizer or are intended for an industrial use.

According to a second means of giving added value to these salts, the aqueous solution of salts is treated by electrodialysis in order to regenerate, on the one hand, ammonia, which is optionally recycled to the neutralization stage, and, on the other hand, sulfuric acid, which, after concentration, is recycled to the stage of hydrolysis of the HMTBN.

According to a third means of giving added value to the salts, the solution of salts, which are essentially composed of ammonium sulfate, is treated by the thermal route in a plant, for example a sulfuric regeneration plant, so as to recover concentrated sulfuric acid which can be recycled directly to hydrolysis of the HMTBN.

An industrial implementation of the combined process is carried out in the following way (cf. FIG. 1).

The neutralized stream (stream 1) is a separated by settling.

The organic phase resulting from the separation by settling is subjected to an operation of release of the salts by a treatment with a phase essentially composed of organic solvent (stream 6). This treatment consists of a liquid-liquid contact. It is carried out in a conventional mixer-settler or in any other liquid-liquid contactor chosen from the following devices: a bank of mixer-settlers, a packed column, a perforated plate column, a rotating disk column, a centrifugal extractor, a pulsed column or any other liquid-liquid contactor.

The extract and the raffinate are separated (stream 4 and stream 12). The raffinate is recycled to the stage of exhaustive extraction of HMTBA from the aqueous phase resulting from the separation by settling. The extract (stream 4) is subjected to a treatment targeted at removing the solvent. The removal is carried out in particular by evaporation, distillation or steam distillation. This removal operation is carried out in order to obtain an HMTBA at the bottom (stream 8) which is highly depleted in residual solvent and which is sufficiently concentrated, before an optional adjustment to the assay. The top stream (stream 5) originating from this removal of solvent is recycled partly to the stage of release with respect to the organic phase resulting from the separation by settling (stream 6)

partly to the stage of exhaustive extraction with respect to the aqueous phase resulting from the separation by settling (stream 7).

The aqueous phase which has been separated by settling (stream 10) is subjected to a treatment for exhaustive extraction of the HMTBA by contact with a phase essentially composed of organic solvent (stream 7). This treatment is also carried out in a liquid-liquid contactor, which can be a bank of mixer-settlers, a packed column, a perforated plate column, a rotating disk column, a centrifugal extractor, a pulsed column or any other liquid-liquid contactor.

The extract and the raffinate are separated (stream 11 and stream 13). The extract (stream 11) is recycled to the stage of release with respect to the organic phase resulting from the separation by settling, whereas the raffinate (stream 13) is subjected to a treatment targeted at removing the solvent. This treatment is in particular a distillation, an evaporation or a stripping. It is preferably carried out during a crystallization of the ammonium sulfate by evaporation.

The present invention will be more fully described with the help of the following examples, which must not be regarded as limiting the invention.

1—Examples of

Liquid-liquid Extraction which is Carried out on the Aqueous Phase after Separation by Settling of the Neutralized Hydrolysis Stream The object of this operation is to extract the residual HMTBA present in the aqueous phase after separation by settling before crystallization of the ammonium sulfate.

The composition of the aqueous phase to be extracted is as follows:

| | |
|---|---|
| [HMTBA] = | 3.7% W/W |
| [WATER] = | 40.9% W/W |
| [salts] = | 55.4% W/W |

Example of Exhaustive Extraction of this Aqueous Phase with MIBK 505.9 grams of this aqueous phase stream were brought into contact in a stirred 1 liter reactor with 56.2 grams of MIBK at a temperature of 75° C. The extraction solvent/ solution to be separated ratio was 11.1% W/W. After separation of the two phases by settling at 75° C., the two phases were withdrawn and analyzed:

The upper phase, in which the HMTBA is partially extracted, represented 67.9 grams and had a load of HMTBA of 20.5% W/W. The content of salts in this upper phase was below the detection limit of the analytical tool (potentiometry).

Thus, 74.3% of the participating HMTBA could be extracted with MIBK in a single stage with a participating organic solvent/solution to be extracted ratio of 11.1%.

The lower phase, for its part, had a load of HMTBA of 0.97% W/W.

The partition coefficient, expressed as follows [HMTBA] upper phase/[HMTBA] lower phase, is 21.1.

2—Example of Exhaustive Extraction of the Aqueous Phase with Ethyl Carbonate 505.9 grams of the aqueous phase were brought into contact in a 1 liter stirred reactor with 56.2 grams of ethyl carbonate at a temperature of 75° C. The extraction solvent/solution to be separated ratio was 11.1% W/W. After separating the two phases by settling at 75° C., the two phases were withdrawn and analyzed:

The upper phase, in which the HMTBA is partially extracted, represented 67.3 grams and had a load of HMTBA of 14.2% W/W. The content of salts in this upper phase was below the detection limit of the analytical tool (potentiometry).

Thus, 50.3% of the participating HMTBA could be extracted with ethyl carbonate in a single stage with a participating organic solvent/solution to be extracted ratio of 11.1%.

The lower phase, for its part, had a load of HMTBA of 1.53% W/W.

The partition coefficient, expressed as follows [HMTBA] upper phase/[HMTBA] lower phase, is 9.3.

3—Example of Exhaustive Extraction of the Aqueous Phase with Methyl Ethyl Ketone 505.9 grams of aqueous phase were brought into contact in a stirred 1 liter reactor with 56.2 grams of MEK at a temperature of 75° C. The extraction solvent/solution to be separated ratio was 11.1% W/W. After separating the two phases by settling at 75° C., the two phases were withdrawn and analyzed:

The upper phase, in which the HMTBA is partially extracted, represented 65.3 grams and had a load of HMTBA of 23.7% W/W. The content of salts in this upper phase was below the detection limit of the analytical tool (potentiometry).

Thus, 82.9% of the participating HMTBA could be extracted with MEK in a single stage with a participating organic solvent/solution to be extracted ratio of 11.1%.

The lower phase, for its part, had a load of HMTBA of 0.6% W/W.

The partition coefficient, expressed as follows [HMTBA] upper phase/[HMTBA] lower phase, is 39.5.

4—Examples of Liquid-liquid Release Carried out on the Organic Phase after Separation by Settling of the Neutralized Hydrolysis Stream The object of this operation is to purify the organic phase from salts (NH4)2SO4 and NH4HSO4) by displacement of these salts into an aqueous phase which is formed by addition of a solvent exhibiting little affinity for water.

The composition of the organic phase resulting from the separation by settling of the neutralized hydrolysis stream is as follows:

| | |
|---|---|
| [HMTBA] = | 66.6% W/W |
| [WATER] = | 22.4% W/W |
| [salts] = | 11% W/W |

Example of Extraction of the Salts by Addition of MIBK 379 grams of this organic phase stream were brought into contact in a 1 liter stirred reactor with 137.3 grams of MIBK at a temperature of 75° C. The extraction solvent/solution to be separated ratio was 36.2% W/W. After separation by settling at 75° C., the two phases formed were withdrawn and analyzed:

The upper phase, in which the HMTBA was extracted, represented 445.7 g and had a load of salts of 1%. Thus, with the participating organic solvent/solution to be treated ratio used, 89% of the salts present in the medium before extraction could be displaced into the aqueous phase created by the addition of MIBK.

The lower phase, into which the salts are partially displaced, represented 70.2 grams and had a load of HMTBA of 2% W/W. Thus, under these displacement conditions, 99.4% of the participating HMTBA could be extracted with MIBK in one stage with a participating organic solvent/solution to be treated ratio of 36.2%.

The lower phase, for its part, had a load of salts of 53% W/W.

The partition coefficient, expressed as follows [salts] lower phase/[salts] upper phase, is 53.

5—Example of Extraction of the Salts by Addition of Ethyl Carbonate 379 grams of the organic phase stream were brought into contact in a stirred 1 liter reactor with 137.3 grams of ethyl carbonate at a temperature of 75° C. The extraction solvent/solution to be separated ratio was 36.2% W/W. After separating by settling at 75° C., the two phases formed were withdrawn and analyzed:

The upper phase, in which the HMTBA was extracted, represented 455.5 g and had a load of salts of 2.4% W/W. Thus, with the participating organic solvent/solution to be treated ratio used, 73.9% of the salts present in the medium before extraction could be displaced into the aqueous phase created by the addition of ethyl carbonate.

The lower phase, into which the salts are partially displaced, represented 60.8 grams and had a load of HMTBA of 2.5% W/W. Thus, under these displacement conditions, 99.4% of the participating HMTBA could be extracted with ethyl carbonate in one stage with a participating organic solvent/solution to be treated ratio of 36.2% W/W.

The lower phase, for its part, had a load of salts of 50.6% W/W. The partition coefficient, expressed as follows [salts] lower phase/[salts] upper phase, is 21.1.

6—Example of Extraction of the Salts by Addition of MEK 379 grams of the organic phase stream were brought into contact in a stirred 1 liter reactor with 137.3 grams of MEK at a temperature of 75° C. The extraction solvent/solution to be separated ratio was 36.2% W/W. After separating by settling at 75° C., the two phases formed were withdrawn and analyzed:

The upper phase, in which the HMTBA was extracted, represented 467 g and had a load of salts of 2.1% W/W. Thus, with the participating organic solvent/solution to be treated ratio under consideration, 76.5% of the salts present in the medium before extraction could be displaced into the aqueous phase created by the addition of MEK.

The lower phase, into which the salts are partially displaced, represented 49.3 grams and had a load of HMTBA of 2% W/W. Thus, under these displacement conditions, 99.5% of the participating HMTBA could be extracted with MEK in one stage with a participating organic solvent/solution to be treated ratio of 36.2% W/W.

The lower phase, for its part, had a load of salts of 64.8% W/W.

The partition coefficient, expressed as follows [salts] lower phase/[salts] upper phase, is 30.9.

What is claimed is:

1. A method for separating 2-hydroxy-4-methylthiobutyric acid (HMTBA) from a 2-hydroxy-4- methylthiobutyronitrile (HMTBN) acid hydrolysate mixture comprising HMTBA and water, comprising the following steps:

neutralizing the mixture with aqueous ammonia wherein the amount of water added to the hydrolysate mixture is sufficient to cause the formation of a separate aqueous phase;

settling the neutralized mixture to obtain an organic phase and an aqueous phase;

separating the organic phase, which comprises HMTBA, water and salts, from the aqueous phase, which comprises HMTBA, water and salts;

releasing the salts from the organic phase with an amount of a first organic solvent which is not very miscible with water by contacting said organic phase with said first organic solvent;

exhaustively extracting the HMTBA from the aqueous phase with an amount of a second organic solvent which is not very miscible with water by contacting said aqueous phase with said second organic solvent; and evaporating said first and second organic solvents, wherein said first and second organic solvents are the same or different, further wherein most of the salts are precipitated from the aqueous phase after the aqueous phase has been separated from the organic phase.

2. A method for separating 2-hydroxy-4-methylthiobutyric acid (HMTBA) from a 2-hydroxy-4-methylthiobutyronitrile (HMTBN) acid hydrolysate mixture comprising HMTBA and water, comprising the following steps:

neutralizing the mixture with aqueous ammonia wherein the amount of water added to the hydrolysate mixture is sufficient to cause the formation of a separate aqueous phase;

settling the neutralized mixture to obtain an organic phase and an aqueous phase;

separating the neutralized mixture into two phases wherein the first phase is the organic phase comprising HMTBA, water and salts and the second phase is the aqueous phase comprising HMTBA, water and salts;

treating the first phase, separately from the second phase, with a first organic solvent to release the salts from the first phase, wherein said first organic solvent is not very miscible with water;

treating the second phase, separately from the first phase, with a second organic solvent to exhaustively extract the HMTBA from the second phase, wherein the second organic solvent is not very miscible with water; and evaporating said first and second organic solvents, wherein said first and second organic solvents are the same or different, further wherein most of the salts are precipitated from the aqueous phase after the aqueous phase has been separated from the organic phase.

3. The method of claim 1, wherein the organic phase is contacted with the first organic solvent in a first container and the aqueous phase is contacted with the second organic solvent in a second container that is separate from said first container.

4. The method of claim 2, wherein said first organic solvent is selected from the group consisting of ketones, aldehydes, ethers, esters, carbonates and alcohols, provided they dissolve the HMTBA.

5. The method of claim 2, wherein said second organic solvent is selected from the group consisting of ketones, aldehydes, ethers, esters, carbonates and alcohols, provided they dissolve the HMTBA.

6. The method of claim 1, wherein the first organic solvent and the second organic solvent are identical.

7. The method of claim 1, wherein the first organic solvent and the second organic solvent are different.

8. The method of claim 1, wherein said first organic solvent is selected from the group consisting of ketones, aldehydes, ethers, esters, carbonates and alcohols, provided they dissolve the HMTBA.

9. The method of claim 8, wherein said first organic solvent is selected from the group consisting of ketones of low molecular weight, ethers and carbonates.

10. The method of claim 9, wherein the first organic solvent is selected from the group consisting of methyl ethyl ketone, methyl isobutyl ketone, methyl tert-butyl ether, diisopropyl ether and diethyl carbonate.

11. The method of claim 1, wherein the amount of the first organic solvent used with respect to the organic phase is greater than 0.3 (w/w).

12. The method of claim 11, wherein the amount of the first organic solvent used with respect to the organic phase is between 0.3 and 1 (w/w).

13. The method of claim 1, wherein the second organic solvent is selected from the group consisting of ketones, aldehydes, ethers, esters, carbonates and alcohols, provided they dissolve the HMTBA.

14. The method of claim 13, wherein the second organic solvent is selected from the group consisting of ketones of low molecular weight, ethers and carbonates.

15. The method of claim 14, wherein the second organic solvent is selected from the group consisting of methyl ethyl ketone, methyl isobutyl ketone, methyl tert-butyl ether, diisopropyl ether and diethyl carbonate.

16. The method of claim 1, wherein the amount of the second organic solvent with respect to the aqueous phase is greater than 0.05 (w/w).

17. The method of claim 16, wherein the amount of the second organic solvent with respect to the aqueous phase is between 0.1 and 0.5 (w/w).

18. The method of claim 1, wherein the exhaustive extraction of HMTBA and the release of the salts are carried out concomitantly and according to a continuous process.

19. The method of claim 1, wherein after the salts have been released from the organic phase, at least a portion of the first organic solvent is separated from the HMTBA and recycled so that it becomes at least a portion of the second organic solvent.

20. The method of claim 1, wherein the salts obtained from the aqueous phase are crystallized.

21. The method of claim 20, wherein the resulting salt crystals are treated by electrodialysis in order to generate ammonia, which is recycled to become part of the aqueous ammonia, and sulfuric acid, which, after concentration, is recycled for use in obtaining the HMTBN acid hydrolysate mixture.

22. The method of claim 20, wherein the resulting salt crystals are thermally treated to recover a sulfuric acid solution which is recycled for use in obtaining the HMTBN acid hydrolysate mixture.

23. A method of using the salts recovered from the aqueous phase in the process of claim 20, comprising the step of applying the salts to soil or plants as fertilizer.

* * * * *